United States Patent [19]

Buyniski et al.

[11] 4,322,427

[45] Mar. 30, 1982

[54] ANALGETIC COMPOSITIONS AND METHODS OF USE

[75] Inventors: Joseph P. Buyniski, Syracuse; Anthony W. Pircio, Manlius, both of N.Y.

[73] Assignee: Bristol-Myers Company, New York, N.Y.

[21] Appl. No.: 254,821

[22] Filed: Apr. 16, 1981

[51] Int. Cl.³ .................... A61K 31/40; A61K 31/485
[52] U.S. Cl. ..................................... 424/260; 424/274
[58] Field of Search ............................... 424/260, 274

[56] References Cited

U.S. PATENT DOCUMENTS

| | | | |
|---|---|---|---|
| 3,752,826 | 8/1973 | Carson | 260/326.3 |
| 3,819,635 | 6/1974 | Pachter et al. | 260/285 |
| 4,207,340 | 6/1980 | Gardocki | 424/317 |
| 4,233,314 | 11/1980 | Gardocki | 424/317 |
| 4,233,315 | 11/1980 | Gardocki | 424/317 |
| 4,233,316 | 11/1980 | Gardocki | 424/317 |
| 4,233,317 | 11/1980 | Gardocki | 424/317 |
| 4,234,601 | 11/1980 | Gardocki | 424/319 |
| 4,237,140 | 12/1980 | Dudzenski | 424/260 |
| 4,242,353 | 12/1980 | Gardocki | 424/274 |
| 4,243,673 | 1/1981 | Capetola et al. | 424/275 |

OTHER PUBLICATIONS

Dobkin et al., Canad. Anaesth. Soc. J., 21, 600–610, (1974).
Pircio et al., Arch Int. Pharmacodyn 235, 116–123, (1978).
Drugs of the Future, 2, 698–701, (1977).

*Primary Examiner*—Stanley J. Friedman
*Attorney, Agent, or Firm*—Richard R. Lloyd

[57] ABSTRACT

A method of producing analgesia by the simultaneous or sequential administration of butorphanol and zomepirac and compositions comprising butorphanol and zomepirac which provide enhanced (synergistic) analgetic potencies.

13 Claims, 2 Drawing Figures

SYNERGISTIC ANALGETIC EFFECTS OF MIXTURES OF BUTORPHANOL AND ZOMEPIRAC

ANALGETIC EFFECTS OF MIXTURES OF CODEINE AND ZOMEPIRAC

ANALGETIC COMPOSITIONS AND METHODS OF USE

BACKGROUND OF THE INVENTION

The relief of pain long has been, and remains, one of the primary aims of medicine. Unfortunately, almost all potent analgetic agents produce at least some degree of reaction other than the desired analgesia, particularly when taken in large doses for moderate to severe pain. Such side effects include dizziness, blurring or dimness of vision, nausea, vomiting, increased or depressed respiratory or pulse rates, and the like. Accordingly, in the use of analgetic agents, there must be taken into account not only the analgetic potency of the particular agent but also its potential side-effect liability. It is known to prescribe mixtures of analgetics even though their activites are merely additive, since side-effects may be reduced by combining analgetics which act by different mechanisms. It is also known that, in some instances, mixtures of two or more analgetic agents potentiate each other's activities. This is particularly desirable since the total amount of drug can be reduced and the side-effects decreased. Thus, there is a continuing search for combinations of analgetic agents which produce an enhanced (synergistic) analgetic effect, in an attempt to find particular combinations which produce maximum analgesia with little or no side-effects.

PRIOR ART (A) U.S. Pat. No. 3,819,635 discloses and claims butorphanol and related compounds, and processes for their preparation. The analgesic and narcotic-antagonist activities of butorphanol in several animal models are given.

(B) A. B. Dobkin et al. in Canad. Anaesth. Soc. J., 21, 600–610 (1974), describe double-blind tests comparing the analgesic activities of butorphanol and morphine in postoperative patients with moderate to severe pain. Their results indicate that butorphanol is on the order of ten times more potent than morphine sulfate.

(C) In Arch. Int. Pharmacodyn., 235, 116–123 (1978), A. W. Pircio et al. describe the results of tests in mice of the analgetic effects of combinations of butorphanol and acetaminophen (APAP). Combinations of butorphanol:APAP of 1:125 and 1:10 exhibited analgetic effects which were greater than were expected from a simple additive effect, i.e. were synergistic. The synergistic effect of the 1:125 combination was statistically significant ($p = <0.001$) while the synergistic effect of the 1:10 combination was not statistically significant ($p = <0.1 > 0.05$).

(D) U.S. Pat. No. 3,752,826 discloses and claims zomepirac and related compounds. The compounds are stated to be antiinflammatory agents.

(E) Drugs of the Future, 2, 698–701 (1977), and references cited therein, describe methods for the preparation of zomepirac and its activity as an antiinflammatory agent as well as an analgesic agent. In tests of its analgesic activity in dental patients, 50 mg and 100 mg doses of zomepirac were found to be significantly better than 650 mg of aspirin.

(F) There are many known anti-inflammatory agents which also have analgesic activity. Combinations of one of these antiinflammatory/analgesic agents with acetaminophen (APAP), producing synergistic analgetic activity, are disclosed in various U.S. Pat. Nos. such as follows:
1. 4,207,340—sulindac plus APAP
2. 4,233,313—indomethacin plus APAP
3. 4,233,314—fenprofen plus APAP
4. 4,233,315—ketoprofen plus APAP
5. 4,233,316—naproxen plus APAP
6. 4,233,317—fenbufen plus APAP
7. 4,234,601—diclofenac plus APAP
8. 4,242,353—indoprofen plus APAP.

(G) U.S. Pat. No. 4,237,140 discloses the synergistic analgetic activities of mixtures of nalbuphine plus APAP in ratios of from about 1:2 to about 1:70. Published European Patent Application 19,282 is equivalent and has substantially the same disclosure.

(H) U.S. Pat. No. 4,243,673 broadly discloses synergistic analgetic compositions comprising a mixture of suprofen and a "non-narcotic analgesic", which is defined therein as an analgesic which affects primarily the peripheral nervous system rather than the central nervous system. The "non-narcotic analgesics" suitable for use are stated to include the salicylates, paraaminophenols and pyrazolons, but the only compositions exemplified or claimed are mixtures of suprofen and APAP.

COMPLETE DESCRIPTION OF THE INVENTION

Figure 1:
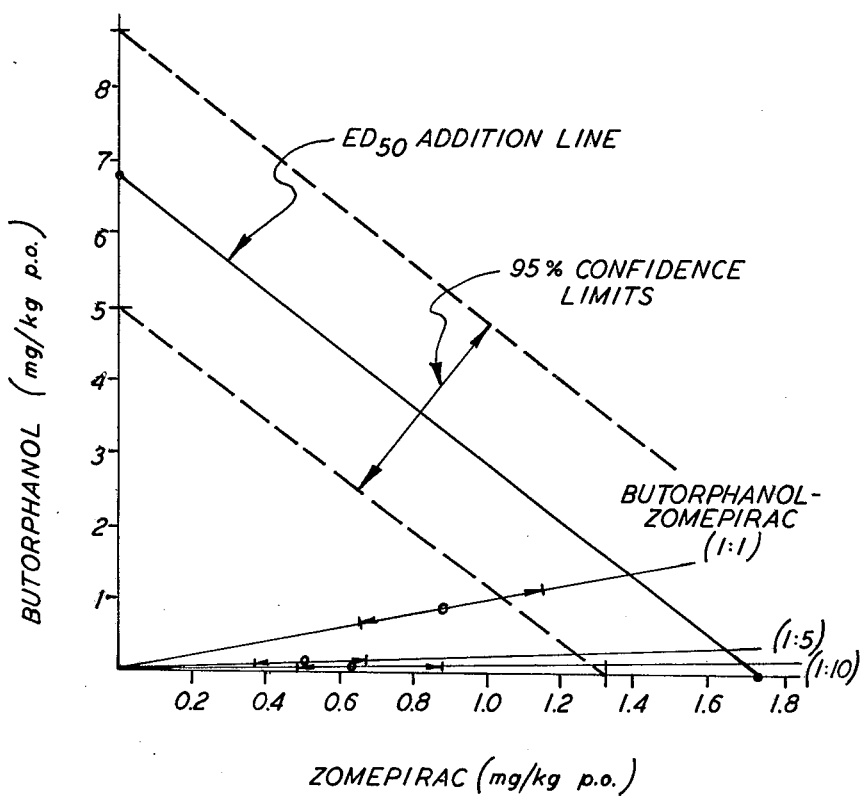
FIG. 1 is an isobolographic analysis showing the synergistic analgetic activities of several mixtures of butorphanol and zomepirac.

In one aspect, this invention relates to a method of producing analgesia in animals, including man, which comprises administering to an animal suffering from pain, either simultaneously or sequentially, butorphanol and zomepirac.

In another aspect, this invention relates to compositions comprising butorphanol and zomepirac which provide enhanced (synergistic) analgetic potencies.

We have surprisingly found that the concomitant administration of the known analgetic agents, butorphanol and zomepirac, in a ratio of from about 1:1 to about 1:100, produces unexpectedly enhanced analgesic activity. The preferred ratios are from about 1:2 to about 1:50, and the most preferred ratios are from about 1:5 to about 1:25. It will be appreciated by those skilled in the art that the enhanced activity will be obtained whether the butorphanol and zomepirac are administered simultaneously as a mixture or sequentially as the two individual components.

Although, for convenience, the simple item "butorphanol" is usually used herein, it is specifically intended that this invention include the use of nontoxic pharmaceutically acceptable acid addition salts of butorphanol. Such salts are well known to those skilled in the art and include, for example, inorganic and organic acid addition salts such as the hydrochloride, hydrobromide, nitrate, sulfate, methanesulfonate, p-toluenesulfonate, succinate, maleate, tartrate and the like. Because of solubility considerations, an acid addition salt of butorphanol is usually preferred over the free base form. Butorphanol tartrate is a particularly preferred acid addition salt.

Similarly, although the simple term "zomepirac" is usually used herein, it is specifically intended that this invention include the use of nontoxic pharmaceutically acceptable salts of zomepirac. This compound contains a carboxylic acid group and and therefore forms salts with organic or inorganic bases. Preferred salts are the sodium and potassium salts.

Butorphanol is the United States Adopted Name for (−)-17-cyclobutylmethyl-3,14-dihydroxymorphinan, and has the structure

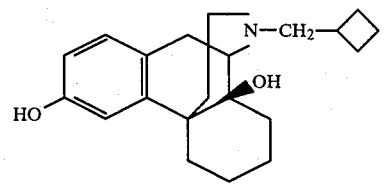

Zomepirac is the United States Adopted Name for 5-(4-chlorobenzyl)-1,4-dimethyl-1H-pyrrole-2-acetic acid, and has the structure

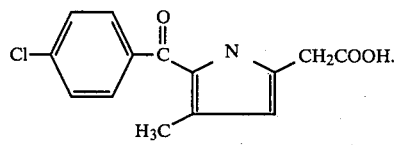

In practicing this invention, the butorphanol and zomepirac may be administered orally or parenterally. For convenience, the oral route is preferred. In preparing the compositions for oral use, any of the usual pharmaceutical media, aids and excipients may be used. For liquid oral preparations, one may utilize water, glycols, oils, alcohols or the like, along with coloring agents, preservatives, flavors or the like, to prepare solutions, elixirs, syrups, suspensions, etc. For solid oral preparations, one may utilize conventional granulating agents, lubricants, binders, disintegrating agents, starches, sugars or the like, to prepare such solid dosage forms as capsules, tablets or powders. In the case of parenteral preparations, the usual form will be a solution of butorphanol and zomepirac in sterile water, along with any desired preservatives or solubility aids.

The dosage of butorphanol and zomepirac to be administered will, of course, vary depending on such factors as the route of administration, age, weight and general health of the patient, severity of the symptoms, kind (if any) of concurrent treatment with other drugs, the frequency of treatment and the effect desired. Usually the dosage of butorphanol will be from about 1 mg to about 20 mg, preferably from about 2 mg to about 10 mg and most preferably about 4 mg. The dosage of zomepirac usually will be from about 10 mg to 500 mg, preferably from about 25 mg to about 250 mg and most preferably from about 50 mg to about 100 mg. Such dosages will be administered from two to five times a day, and usually three or four times a day. If the composition is formulated in a sustained release form, fewer daily doses may be required, depending on the particular formulation.

It is particularly advantageous and convenient to formulate the compositions of butorphanol and zomepirac in unitary dosage form, i.e. physically discrete units which each contain the quantity of butorphanol and zomepirac calculated to produce the desired result, together with any desired pharmaceutical carrier. Such unitary dosage forms may be in the form of capsules, tablets, pills, ampouls, teaspoonsful, tablespoonsful and the like.

TESTS FOR ASSESSING ANALGETIC ACTIVITY

The drugs used in this study were butorphanol tartrate, zomepirac sodium and codeine phosphate. Mixtures were prepared for isobolographic study by combining aliquots of standard solutions of the above drugs. All solutions were freshly prepared with distilled water.

The study of the analgetic activities of butorphanol-zomepirac and codeine-zomepirac combinations, as well as the individual drugs, was done in the mouse (phenylquinone-induced writhing test) following oral administration. The analgetic interaction was investigated by the determination of the oral $ED_{50}$'s (Effective Dose$_{50}$) and the use of the isobolographic method of Loewe [S. Loewe, Arzneim. Forsch., 9, 429–456 (1959)] as modified by Gessner and Cabana [P. K. Gessner and B. E. Cabana, J. Pharmacol. Exp. Ther., 174, 247–259 (1969)].

The fixed ratio method was used to study the interaction of these analgetic drugs. In this procedure the $ED_{50}$ of binary mixtures of butorphanol-zomepirac and codeine-zomepirac were determined by administering various doses of the two drugs in a mixture at a constant ratio. Thus, using the isobolographic analysis of Loewe, it can be determined whether the observed $ED_{50}$'s were significantly different from those expected on the basis of the effects of the individual drugs, and whether this interaction represented synergistic, antagonistic or additive action.

The numerical estimation of the $ED_{50}$ values and their confidence limits was obtained by the probit method of Finney [D. J. Finney, Probit Analysis, pp. 50–80, 230–268, University Press, Cambridge, England, 3rd Ed., (1971)]. The evaluation of the mixture data was performed by techniques described by Finney for the simple (additive) model for similar action.

Antagonism of abdominal writhing in mice was used to evaluate analgetic activity. The method was essentially that described by Siegmund et al. [E. Siegmund et al., Proc. Exp. Biol. Med., 95, 729–731 (1957)]. Swiss-Webster male mice were used which weighed 18–20 gm after an overnight fast. All drugs and binary mixtures were administered orally 25 minutes prior to the intraperitoneal injection of phenylquinone (2 mg/kg). The test materials were given by gavage as a single intubation in a volume of distilled water which was in constant proportion to the body weight (10 ml/kg). Beginning five minutes after the phenylquinone injection, the animals were observed for abdominal writhing and the number of writhes over a ten minute period was counted. An animal was considered to be exhibiting analgesia if the number of writhes exhibited by the animal was 50% or less of the average number of writhes of the saline controls. The $ED_{50}$ values were the doses which produced analgesia in 50% of the treated mice and were calculated from dose-response curves based on at least four dose levels. At least 30 mice were used at each dose level.

Figure 2:
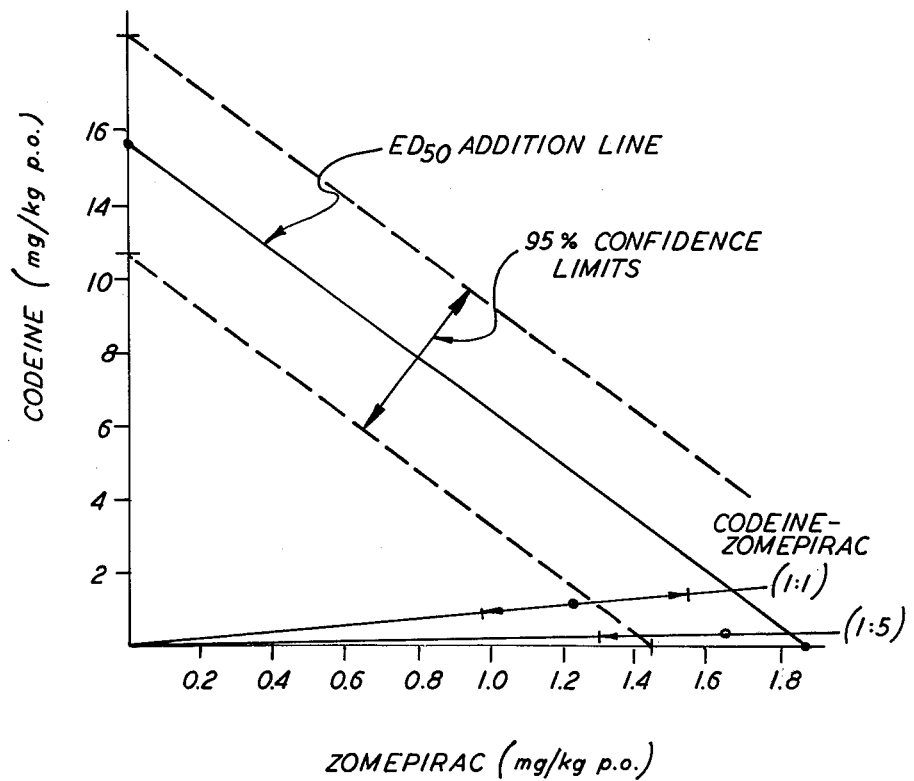
FIG. 2 is an isobolographic analysis showing the additive (non-synergistic) analgetic activities of mixtures of codeine and zomepirac.

The isobolograms showing the interaction of butorphanol-zomepirac and codeine-zomepirac combined in various ratios are shown in FIGS. 1 and 2, respectively. In the case of butorphanol-zomepirac, it may be seen that most of the ED$_{50}$ values of the various mixtures are displaced well below the ED$_{50}$ addition line. However, the ED$_{50}$ values for the codeine-zomepirac combinations are not displaced significantly below the ED$_{50}$ addition line. These data indicate that the various butorphanol-zomepirac combinations were synergistic in that a dose of the mixture smaller than expected achieved a 50% analgetic response, while the codeine-zomepirac combinations produced essentially additive analgetic responses.

A comparison of the observed and expected ED$_{50}$ values are shown in Table 1, along with the results of the statistical treatment of the data. The "observed" ED$_{50}$ of the combinations is that determined experimentally while the "expected" ED$_{50}$ of the combinations is that based on an additive effect of the two ingredients, i.e. is the point of intersection of the ED$_{50}$ addition line with the line which corresponds to the particular ratio of the butorphanol-zomepirac or codeine-zomepirac mixture. Statistically significant synergism was observed with butorphanol-zomepirac combinations of 1:100, 1:50, 1:10 and 1:5, respectively, with synergism of borderline significance (55%) shown by the 1:1 mixture. The codeine-zomepirac combinations of 1:1 and 1:5, respectively, did not produce significant synergism, but resulted in a substantially algebraic summation of their individual analgetic effects.

For comparative purposes, tests such as described above were also conducted on mixtures of butorphanol with suprofen, ibuprofen, naproxen, sulindac, piroxicam and voltaren, respectively. Only the butorphanol-suprofen mixtures showed clearly significant synergism at all ratios tested. The mixtures of butorphanol with ibuprofen, naproxen, sulindac, piroxicam and voltaren, respectively, showed significant synergism at some ratios but to a much lesser degree than the mixtures of butorphanol with zomepirac or suprofen. The results of these tests are shown in Table 2.

TABLE 1

Comparison of Expected and Observed Analgetic ED$_{50}$ Values in the Mouse

| Test Agents Alone and in Mixture | Oral ED$_{50}$ in mg/kg[1] (95% confidence limits) Observed | Expected | % Synergism[2] ± Standard Error | Significance[3] |
|---|---|---|---|---|
| Butorphanol Tartrate | 6.8(5.2–9.0) | — | — | — |
| Zomepirac Sodium | 1.7(1.3–2.3) | — | — | — |
| Butorphanol Tartrate: Zomepirac Sodium | | | | |
| 1:1 | 1.8(1.4–2.4) | 2.8 | 55 ± 19 | Borderline |
| 1:5 | 0.6(0.5–0.8) | 2.0 | 230 ± 21 | <0.001 |
| 1:10 | 0.7(0.5–0.9) | 1.9 | 161 ± 21 | <0.001 |
| 1:50 | 0.6(0.5–0.8) | 1.8 | 183 ± 19 | <0.001 |
| 1:100 | 1.1(0.8–1.4) | 1.7 | 61 ± 21 | <0.05 |
| Codeine Phosphate | 13.7(11.0–16.9) | — | — | — |
| Zomepirac Sodium | 1.9(1.5–2.4) | — | — | — |
| Codeine Phosphate: Zomepirac Sodium | | | | |
| 1:1 | 2.4(1.9–3.1) | 3.3 | 36 ± 17 | Not signif. |
| 1:5 | 2.0(1.6–2.5) | 2.2 | 12 ± 17 | Not signif. |

[1]ED$_{50}$ is expressed in terms of total dose of the mixture.
[2]Percent synergism = $(10^{M_s} - 1)100$, where $M_s = \dfrac{A_3 - A_1}{b} - \log_{10}(\pi 1 \pm R\pi_2)$ (Equation 11.15 of Finney supra)
[3]The p value denotes the significance of the departure between the observed potency and the expected potency.

TABLE 2

Comparison of Expected and Observed Analgetic ED$_{50}$ Values in the Mouse

| Test Agents Alone and in Mixture | Oral ED$_{50}$ in mg/kg[1] (95% confidence limits) Observed[2] | Expected[2] | % Synergism[2] ± Standard Error | Significance[3] (p) |
|---|---|---|---|---|
| Butorphanol Tartrate | 7.4(5.7–9.9) | — | — | — |
| Suprofen | 5.2(3.8–6.9) | — | — | — |
| Butorphanol Tartrate: Suprofen | | | | |
| 1:1 | 2.5(2.0–3.2) | 6.2 | 144 ± 18 | <0.001 |
| 1:5 | 1.7(1.3–2.3) | 5.4 | 212 ± 22 | <0.001 |
| 1:10 | 1.5(1.1–2.0) | 5.3 | 254 ± 21 | <0.001 |
| 1:50 | 1.7(1.3–2.2) | 5.3 | 210 ± 20 | <0.001 |
| Butorphanol Tartrate | 6.8(5.1–9.1) | — | — | — |
| Ibuprofen | 8.1(6.0–10.9) | — | — | — |
| Butorphanol Tartrate: | | | | |

TABLE 2-continued

Comparison of Expected and Observed Analgetic $ED_{50}$ Values in the Mouse

| Test Agents Alone and in Mixture | Oral $ED_{50}$ in mg/kg[1] (95% confidence limits) Observed[2] | Expected[2] | % Synergism[2] ± Standard Error | Significance[3] (p) |
|---|---|---|---|---|
| Ibuprofen | | | | |
| 1:1 | 6.3(4.6–8.7) | 7.4 | 17 ± 20 | Not signif. |
| 1:5 | 4.8(3.6–6.4) | 7.9 | 64 ± 22 | <0.05 |
| 1:10 | 5.1(3.7–6.9) | 8.0 | 56 ± 23 | Borderline |
| 1:50 | 5.6(4.3–7.6) | 8.1 | 43 ± 22 | Not signif. |
| 1:100 | 5.6(4.1–7.5) | 8.1 | 45 ± 21 | Not signif. |
| Butorphanol Tartrate: | 6.8(5.2–8.9) | — | — | — |
| Naproxen | 9.5(7.3–12.2) | — | — | — |
| Butorphanol Tartrate: Naproxen | | | | |
| 1:1 | 7.0(5.5–9.0) | 7.9 | 13 ± 17 | Not signif. |
| 1:10 | 6.3(4.8–8.2) | 9.1 | 46 ± 17 | <0.05 |
| 1:50 | 6.0(4.7–7.4) | 9.4 | 57 ± 20 | <0.05 |
| Butorphanol Tartrate | 7.2(5.2–9.8) | — | — | — |
| Sulindac | 15.4(11.1–21.4) | — | — | — |
| Butorphanol Tartrate: Sulindac | | | | |
| 1:1 | 8.8(6.2–12.9) | 9.8 | 10 ± 26 | Not signif. |
| 1:5 | 9.0(6.4–13.1) | 12.9 | 44 ± 24 | Not signif. |
| 1:10 | 9.0(6.5–12.9) | 13.9 | 50 ± 29 | Not signif. |
| 1:50 | 8.9(6.5–12.3) | 15.1 | 69 ± 26 | <0.05 |
| 1:100 | 9.7(6.9–13.8) | 15.2 | 53 ± 27 | Borderline |
| Butorphanol Tartrate | 6.4(4.7–8.6) | — | — | — |
| Piroxicam | 1.6(1.1–2.2) | — | — | — |
| Butorphanol Tartrate: Piroxicam | | | | |
| 1:5 | 1.5(1.1–2.2) | 1.9 | 21 ± 26 | Not signif. |
| 1:10 | 1.3(0.9–1.8) | 1.7 | 36 ± 27 | Not signif. |
| 1:20 | 1.0(0.7–1.3) | 1.7 | 74 ± 26 | <0.05 |
| 1:50 | 1.1(0.7–1.5) | 1.6 | 53 ± 29 | Not signif. |
| Butorphanol Tartrate | 6.5(5.0–8.5) | — | — | — |
| Voltaren | 4.4(3.3–5.9) | — | — | — |
| Butorphanol Tartrate: Voltaren | | | | |
| 1:1 | 4.2(3.1–5.5) | 5.3 | 26 ± 19 | Not signif. |
| 1:10 | 2.4(1.8–3.1) | 4.6 | 93 ± 22 | <0.02 |
| 1:50 | 3.3(2.4–4.5) | 4.5 | 35 ± 23 | Not signif. |

We claim:

1. An analgetic composition consisting essentially of (a) butorphanol or a nontoxic pharmaceutically acceptable acid addition salt thereof and (b) zomepirac or a nontoxic pharmaceutically acceptable salt thereof, wherein the weight ratio of (a) to (b) is from about 1:1 to about 1:100.

2. A composition of claim 1 wherein the weight ratio of (a) to (b) is from about 1:2 to about 1:50.

3. A composition of claim 1 wherein the weight ratio of (a) to (b) is from about 1:5 to about 1:25.

4. A composition of claim 1, 2 or 3 which contains in addition a pharmaceutically acceptable carrier.

5. A composition of claim 1, 2 or 3 wherein the butorphanol is present as the tartrate salt and the zomepirac is present as the sodium salt.

6. A composition of claim 5 which contains in addition a pharmaceutically acceptable carrier.

7. An analgetic composition in unitary dosage form which comprises from about 1 to about 20 mg of butorphanol or a nontoxic pharmaceutically acceptable acid addition salt thereof and from about 10 mg to about 500 mg of zomepirac or a nontoxic pharmaceutically acceptable salt thereof, plus a pharmaceutically acceptable carrier.

8. A composition of claim 7 wherein the butorphanol or salt thereof is present in an amount of from about 2 mg to about 10 mg and the zomepirac or salt thereof is present in an amount of from about 25 mg to about 250 mg.

9. A composition of claim 7 wherein the butorphanol or salt thereof is present in an amount of 4 mg and the zomepirac or salt thereof is present in an amount of from about 50 mg to about 100 mg.

10. A composition of claim 7, 8 or 9 wherein the butorphanol is present as the tartrate salt and the zomepirac is present as the sodium salt.

11. A method of producing analgesia in an animal which comprises administering to said animal, simultaneously or sequentially, an effective analgetic amount of (a) butorphanol or a nontoxic pharmaceutically acceptable acid addition salt thereof and (b) zomepirac or a nontoxic pharmaceutically acceptable salt thereof, wherein the weight ratio of (a) to (b) is from about 1:1 to about 1:100.

12. A method of producing analgesia in an animal which comprises administering to said animal an effective analgetic amount of a composition of claim 4.

13. A method of producing analgesia in an animal which comprises administering to said animal an effective analgetic amount of a composition of claim 6.

* * * * *